United States Patent [19]

Harryman

[11] Patent Number: 5,207,380
[45] Date of Patent: May 4, 1993

[54] IRRIGATION CONTROL SYSTEM

[76] Inventor: Frank Harryman, 2131 Midvale Ave., Westwood, Calif. 90025

[21] Appl. No.: 841,427

[22] Filed: Feb. 26, 1992

[51] Int. Cl.$^5$ .............................................. A01G 25/16
[52] U.S. Cl. ........................................ 239/64; 239/70; 137/78.3
[58] Field of Search ........................ 239/63, 64, 67, 69, 239/70; 137/78.3

[56] References Cited

U.S. PATENT DOCUMENTS

| | | |
|---|---|---|
| 2,796,291 | 6/1957 | Mueller . |
| 3,590,335 | 6/1971 | Tetar . |
| 3,991,939 | 11/1976 | Maclay . |
| 4,190,884 | 2/1980 | Medina . |
| 4,194,691 | 3/1980 | Birnbach et al. . |
| 4,197,866 | 4/1980 | Neal . |
| 4,256,133 | 3/1981 | Coward et al. ...................... 239/64 |
| 4,304,989 | 12/1981 | Vos et al. . |
| 4,333,490 | 6/1982 | Enter, Sr. .............................. 239/64 |
| 4,396,149 | 8/1983 | Hirsch .................................. 239/64 |
| 4,541,563 | 9/1985 | Uetsuhara ............................ 239/64 |
| 4,548,225 | 10/1985 | Busalacchi ........................... 239/64 |
| 4,657,039 | 4/1987 | Bireley et al. ..................... 137/78.3 |
| 4,683,904 | 8/1987 | Iltis ...................................... 239/64 |
| 4,796,654 | 1/1989 | Simpson .............................. 239/64 |
| 4,838,296 | 6/1989 | Brooks . |
| 4,892,113 | 1/1990 | Fattahi ................................. 239/64 |
| 4,993,640 | 2/1991 | Baugh . |

Primary Examiner—Gregory L. Huson
Assistant Examiner—Karen B. Merritt
Attorney, Agent, or Firm—Poms, Smith, Lande & Rose

[57] ABSTRACT

A system is disclosed comprised of several inputs in the soil that send a current into the soil and measure the resulting resistance in the soil. The soil resistance varies inversely with the level of moisture in the soil. Two voltage comparators are used to determine whether the soil has reached a pre-determined level of saturation or dryness. If the pre-determined level of dryness is exceeded, then a signal is sent through a switch and a latch, and activates the sprinkler solenoids. Once the pre-determined level of saturation is reached, a saturated signal is sent through the switch and latch in order to de-energize the solenoids. The system includes an over-watering prevention feature wherein a clock circuit is used so as to pulse the sprinklers in order to allow the water to permeate the soil between the sprinkler pulses.

19 Claims, 3 Drawing Sheets

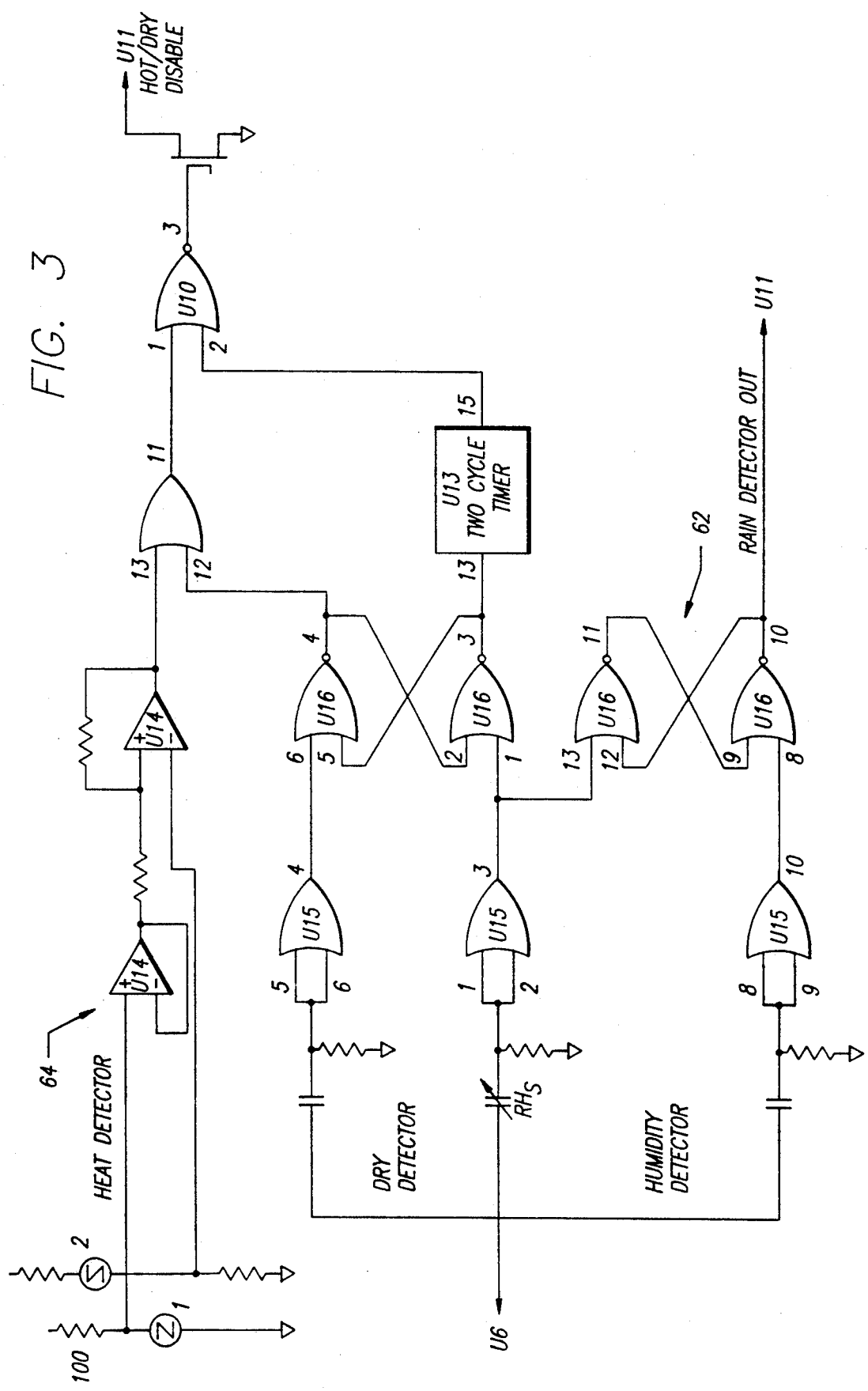

IRRIGATION CONTROL SYSTEM

I. FIELD OF INVENTION

This invention relates to an irrigation control system and more particularly to an irrigation control system wherein an alternating current is applied to moisture sensors in the soil, and a circuit is coupled to the sensors to measure the moisture in the soil and pulse the corresponding sprinkler valves in response to a low soil moisture measurement.

II. BACKGROUND OF INVENTION

Irrigation control systems and sprinkler control systems are known in the art. Some of the known sprinkler and irrigation control systems are operated manually. Many of the known irrigation or sprinkler control systems utilize timers to activate and deactivate the sprinkler valves. These timers are either mechanically or electrically operated, and activate the sprinkler valves at a predetermined time for a predetermined period of time. A disadvantage of this type of automatic sprinkler control system is that the system does not account for the level of moisture present in the soil before the sprinklers are activated. Therefore, the sprinkler valves activate whether or not the soil requires watering. For example, the sprinkler valves will automatically activate during a rainstorm, even though the soil does not require watering. Also, because the sprinkler valves turn off automatically after a predetermined amount of time, the soil may not be adequately watered before the sprinklers are deactivated.

The timer controlled sprinkler and irrigation control systems therefore, are inefficient in at least three ways. Firstly, the landscaping is not properly irrigated or watered. Instead, the landscaping is frequently either underwatered or overwatered. Secondly, if the sprinkler valves are activated when the soil is already sufficiently moist, the water from the sprinkler valves creates run-off and water waste.

Thirdly, with most automatic sprinkling systems, the water is applied to the ground faster and in a greater quantity than the ground is capable of absorbing. As a result, many automatic sprinklers create run-off or flooding even when used under ideal conditions. The second and third above-described problems are especially of concern in geographical regions suffering from water shortages or drought.

In order to overcome these problems with the timer controlled sprinkler systems, automatic sprinkling control systems that include soil moisture probes were designed. These systems use probes inserted into the soil to measure moisture in the ground. The soil moisture sensors measure either the resistance or the capacitance level in the soil, which corresponds to the level of moisture in the soil. The sprinkler valves are activated when the probe detects a lack of moisture, and the sprinkler valves are deactivated when sufficient soil moisture is detected.

However, the soil moisture probe sprinkler control systems are also subject to certain disadvantages due to the inefficiencies of the soil moisture sensors. Firstly, the soil moisture sensors, in order to properly measure the soil moisture content, are inserted to a certain depth into the soil. However, the water from the sprinkler valves requires a significant period of time to soak from the top surface of the ground down into the soil. Depending on the depth of insertion for the soil moisture probes, it may require several minutes for the water to soak into the soil surrounding the contacts. As a result, by the time the soil moisture probes detect a sufficient level of moisture, the ground has already been overwatered for several minutes. This problem creates overwatering, water waste, and water run-off.

A second disadvantage of many of the soil moisture sensors used in the prior irrigation control systems is that the system applies a direct voltage across the sensors in order to measure the level of resistance or capacitance in the soil. The application of direct current to the sensors causes electrolysis and hydrolysis at the sensor. The hydrolysis and electrolysis effect breaks the bond between hydrogen and oxygen in the soil moisture. In turn, the hydrogen ion both causes conduction and enhances the ionization of chloride in the salts in the soil. Therefore, after time, the direct current type of sensor is not sensing water, but the ionized salts. Furthermore, the ionized salts are not necessarily proportional to the moisture in the soil in that region. The buildup due to electrolysis adjacent the sensor tends to increase the electrical transmissivity of that portion of the soil due to ionization. This increase in ionization in that region disturbs the reading so that the direct current through the probe is not proportional to the water moisture. As a result, the current stays the same while the soil becomes less moist over a period of time. Eventually, the sensor becomes conductive even though the soil is quite dry in the region of the sensor. Therefore the use of direct current with the soil moisture sensors is not reliable over an extended period of time.

Moreover, the soil moisture sensor sprinkling systems have not solved the problem wherein water is applied to the ground faster than the ground can absorb the water. Therefore, the soil moisture sensor systems can still result in undesired run-off, flooding, and water waste.

Therefore, a need exists for an improved irrigation control system that applies alternating current to soil moisture sensors to determine whether the soil has reached a pre-determined level of saturation or dryness, and pulses the sprinklers when the pre-determined level of soil dryness is reached, and deactivates the sprinklers when a predetermined level of soil saturation is reached.

III. SUMMARY OF INVENTION

One object of the present invention is to provide an improved irrigation control system wherein soil moisture sensors are utilized to activate and deactivate the sprinklers.

A still further object of the invention is to provide an improved irrigation control system wherein the sprinklers are pulsed in order to allow the water to drain into the ground between sprinkler pulses.

Another object of the present invention is to provide an improved irrigation control system wherein alternating current is applied to the moisture sensors to measure the resistance and corresponding moisture level of the soil.

Yet another object of this invention is to provide an improved irrigation control system that only allows watering after sunset and before sunrise.

Another object of this invention is to provide an improved irrigation control system wherein the area is divided into zones, and only the zones requiring irrigation are irrigated.

A further object of the present invention is to provide an improved irrigation control system wherein the system automatically deactivates when rain is detected.

Another object of the present invention is to provide an improved irrigation control system wherein the system automatically undergoes a sprinkling cycle when a predetermined degree of ambient heat is detected.

These and other objects of the present invention are achieved through an irrigation control device comprising a sprinkler valve, a soil moisture sensor for measuring the level of moisture in the soil surrounding the sensor, and circuit means responsive to the sensor for initiating a sprinkler cycle when the soil moisture sensor detects a low soil moisture level, and repeating the cycle until the sensor detects a saturated soil condition, and further wherein the sprinkler cycle is comprised of the activation of the sprinkler valve for a first predetermined time period, and a subsequent deactivation of the sprinkler valve for a second predetermined period of time.

More specifically, the objects of the present invention are achieved through a multichannel irrigation control system for an area having a plurality of zones, wherein the system comprises a plurality of sprinkler valves, wherein at least one of the sprinklers is located in each of the zones. The system includes a plurality of soil moisture sensors, wherein at least one of the sensors is located in each of the zones. The system also includes an input selector for sequentially selecting one of the soil moisture sensors as a selected sensor, means for applying current to the selected sensor, means for measuring a resultant current from the selected sensor, a current to voltage converter for converting the resultant current to a converted voltage, a dry threshold voltage comparator for comparing the converted voltage level to a predetermined high voltage level, and producing a dry signal when the voltage is higher than the predetermined high signal, a saturated threshold voltage comparator for comparing the converted voltage level to a predetermined low voltage level, and producing a saturated signal when the voltage is lower than the predetermined low voltage, means for storing the dry signal and the saturated signal for the selected sensor, means for scanning the status of the latch, and means for initiating a sprinkler cycle in response to reading a scanned stored dry signal, and repeating the cycle until a saturated signal is read. The sprinkler cycle of the system is comprised of activation of the sprinkler valve for a first predetermined period of time, and a subsequent deactivation of the sprinkler valve for a second predetermined period of time.

These and other objects of the present invention will now become apparent from a review of the drawings and the following description of the preferred embodiments.

IV. BRIEF DESCRIPTION OF THE DRAWINGS

FIG. 3 is an electrical schematic of the hot weather detector and the rain detector of the multichannel irrigation control system of the present invention.

V. DETAILED DESCRIPTION

Figure 1:
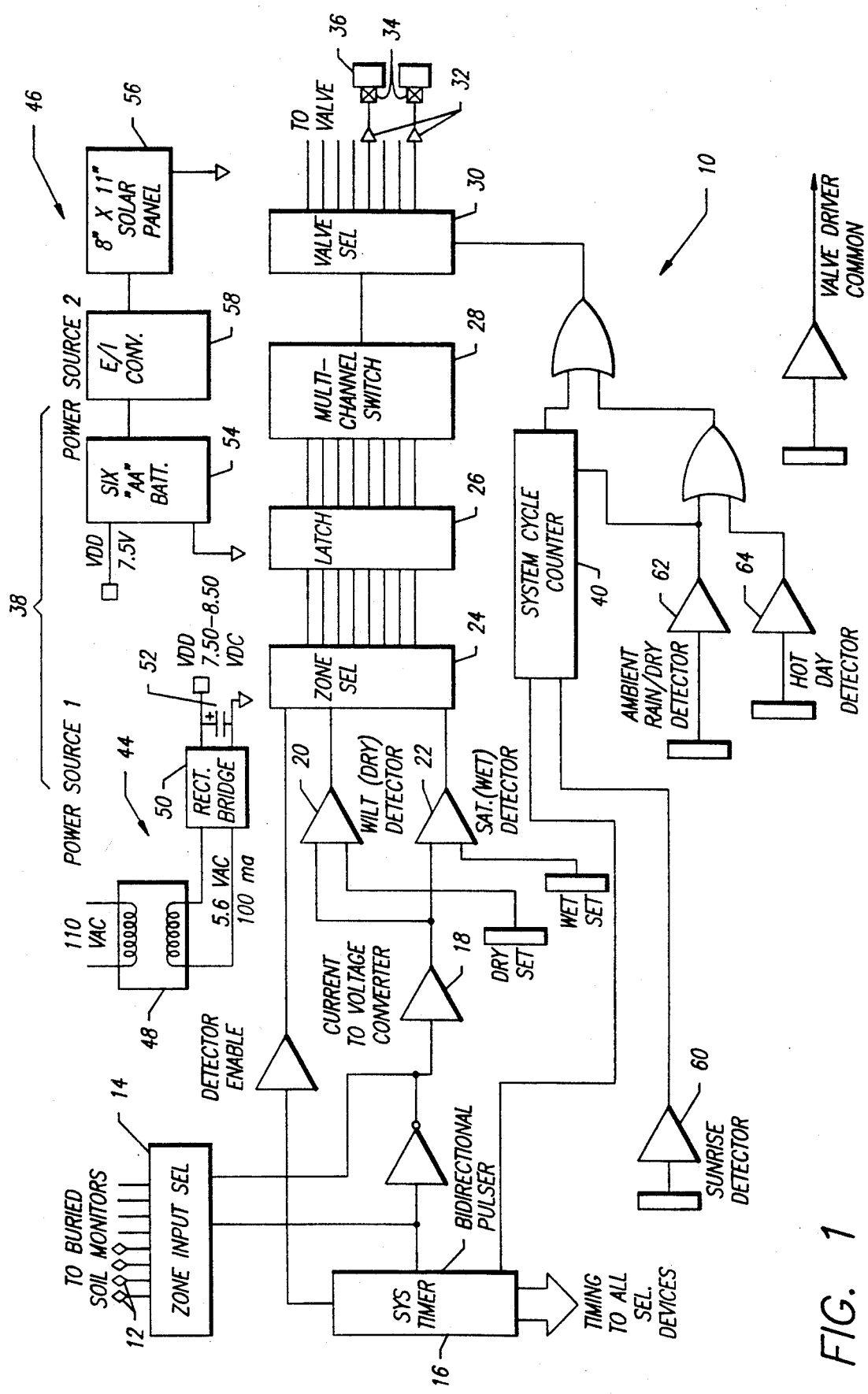
FIG. 1 is a block diagram of one embodiment of the irrigation control system of this invention.

Referring now to FIG. 1, one embodiment of a multi-channel irrigation control system 10 is shown in block diagram form. The multi-channel irrigation system shown is primarily comprised of a plurality of soil moisture sensors 12, and input selector 14, a timing and pulse generator 16, a current to voltage converter 18, a dry soil comparator 20, a saturated soil comparator 22, a zone selector 24, a latch 26, a multichannel switch 28, a valve selector 30, a plurality of valve drivers 32, a plurality of sprinkler valves, 34, a plurality of sprinklers 36, and a power supply 38.

Figure 2:
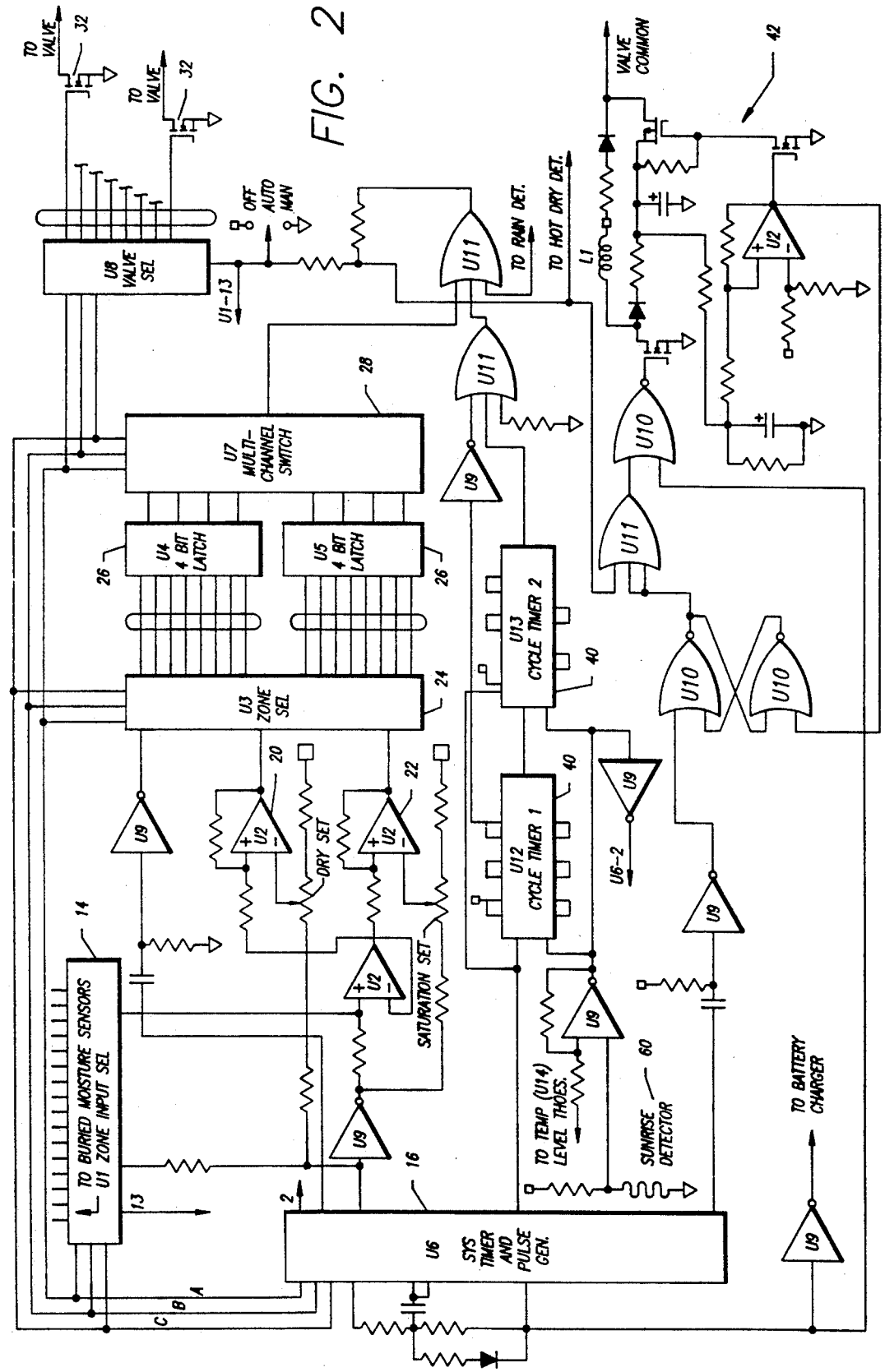
FIG. 2 is an electrical schematic of a multi-channel irrigation control system of the present invention.

Referring now to FIGS. 1 and 2, the operation of the multi-channel irrigation control system 10 is described. The multi-channel irrigation control system 10 may be used in an area that is divided into several zones. Each zone has at least one soil moisture sensor 12 buried in the soil, and at least one sprinkler 36 corresponding to the soil moisture sensor 12. The soil moisture sensor 12 is located in close proximity to the corresponding sprinkler 36. Because each zone has a separate soil moisture sensor 12 and corresponding sprinkler 36, the soil moisture level of each zone is independently controlled, providing for more precise irrigation control.

The soil moisture sensors 12 are preferably each comprised of two spaced apart conductive plates. However, if the system is used in connection with potted plants, the sensor 12 may be optionally comprised of three wires. An alternating current is applied to the conductive plates, and the resulting current is measured. The measured current is inversely related to the level of resistance in the soil surrounding the sensor 12. The level of resistance in the soil is also inversely related to the level of moisture in the soil. Therefore, as the level of moisture decreases, the level of resistance increases, and the measured current decreases. As the level of moisture increases, the level of resistance decreases, and the measured current increases.

The input selector 14 is preferably an input device with a multi-channel switch to switch between the sensors 12. A bidirectional current is applied through the input selector 14 sequentially to each of the soil moisture sensors 12. The measured current is then converted to voltage by the current to voltage converter 18. The converted voltage from the converter 18 is then preferably buffered. The converted voltage is then applied to the dry soil comparator 20 and the saturated soil comparator 22. The dry soil comparator 20 compares the converted voltage to a predetermined high voltage level. If the converted voltage exceeds the predetermined high voltage level, the dry soil comparator 20 sends a dry soil signal to the latch 26 through the zone selector 24.

The saturated soil comparator 22 compares the converted voltage to a predetermined low voltage level. If the converted voltage is lower than the predetermined low voltage level, the saturated soil comparator 22 sends a saturated soil signal to the latch 26 through the zone selector 24. The latch 26 stores the data from the comparators 20 and 22.

The latch 26 is shown in FIG. 2 as comprising two separate 4-bit latches. In this embodiment, each separate 4-bit latch comprises four set-reset flip-flops. The zone selector 24 is strobed by the timing and pulse generator 16 so that the system only interrogates the zone selector data at periodic intervals. Therefore, the latch 26 can only changes states when the zone selector 24 is strobed. The multi-channel switch 28 scans the status of the latch 26, and in response to the data in the latch 26, sends a signal to the output multiplexer 30, which drives a valve driver 32 corresponding to the appropriate sprinkler valves 34 for the selected sensor 12. An important feature of the present invention is the pulsing of the sprinkler cycle. The system timing and pulse generator 16 controls the sprinkler cycle for the irrigation control system 10. The system timing and pulse generator 16 addresses the sprinkler valves 34, and cause the valves 34 to be activated for a present period of time, then subsequently deactivated for a preset period of time. The purpose of the pulsed sprinkling cycle is to allow the water to soak into the ground before the subsequent soil moisture readings. As a result, the soil moisture readings are more accurate because the water has soaked into the ground to the area surrounding the soil moisture sensors 12. Additionally, the ground is capable of absorbing the water dispersed from the sprinklers during the predetermined period of time for sprinkler activation, and therefore the subsequent deactivation of the sprinklers 36 for the predetermined period of time prevents water run-off.

In the sprinkling cycle of the preferred embodiment, the sprinklers 36 are activated for approximately one and one half minutes, and are subsequently deactivated for approximately ten minutes. However, these predetermined time periods will vary according to the ambient environmental and soil conditions.

If, after the ten minutes of sprinkler deactivation, the converted voltage remains higher than the predetermined low voltage level, the pulsed sprinkling cycle of approximately one and one half minutes of sprinkler activation and ten minutes of sprinkler deactivation is repeated. The cycle is therefore repeated until the predetermined low voltage level is reached, indicating soil saturation. Upon reaching soil saturation, the latch 26 corresponding to the selected soil moisture sensor is set, preventing further repetition of the watering cycle in that zone until the converted voltage exceeds the high voltage level, indicating dry soil.

The multichannel irrigation control system 10 further includes a system cycle counter 40. The system cycle counter 40 is coupled to the timing and pulse generator 16, and determines when the output multiplexer 30 is interrogated to determine whether the initiation of the sprinkler cycle is necessary.

The system 10 also includes a boost circuit 42. The boost circuit 42 provides for low power operation of the sprinkler valves 34. In the boost circuit 42, each of the valves 34 is activated by discharging a capacitor into the valve solenoid. After the valve solenoid is pulled in, only a small holding current is required to maintain operation of the valves. Therefore, the boost circuit 42 reduces the current requirement for operating the sprinkler valves 34.

Another feature of the irrigation control system 10 is a sunrise detector circuit 60. The sunrise detector circuit 60 disables the system 10 during daylight hours, after sunrise and before sunset. Therefore, the sunrise detector circuit 60 prevents sprinkling during hours when the sun will cause evaporation of the water before the water can soak into the ground.

The system 10 is operated by the power supply 38. The system may be run off of an AC power supply 44 or a DC power supply 46. The AC power supply 44 is preferably comprised of a 110 VAC to 4.6 VAC transformer 48 with a bridge rectifier 50 and filter capacitor 52. The DC power supply 46 is preferably comprised of a plurality of Nickel Cadium batteries 54 with a solar powered battery charger 56 and voltage to current converter 58. The solar powered battery charger 56 includes an approximately eight inch by eleven inch solar panel.

Referring now to FIG. 3, the electrical schematic for additional features of the multi-channel irrigation control system is shown. One feature is the rain detector circuit 62, wherein the system 10 is automatically disabled when rainfall is detected. Another feature shown in FIG. 3 is a heat detector circuit 64. The heat detector circuit 64, in response to the detection of hot, dry ambient conditions, initiates at least one sprinkler cycle. In the preferred embodiment, the heat detector circuit 64 initiates two sprinkler cycles in response to the detection of hot, dry ambient conditions. The heat detector circuit therefore prevents the wilting and drying of the plants caused by the sun when the soil is still adequately moist.

The multichannel irrigation control system 10 is capable of driving AC or DC sprinkler valves, and allows for simple integration with existing sprinkler systems. The electrical controls of the system may be contained in a package approximately three inches by five inches and three inches deep.

Having thus described exemplary embodiments of the present invention, it should be noted by those skilled in the art that the within disclosures are exemplary only and that various other alternatives, adaptations and modifications may be made within the scope of the invention. Thus by way of example, but not of limitation, the circuit means for initiating the sprinkler cycle when the soil moisture sensor detects a low soil moisture level may vary. Also, the timing of the sprinkler cycle may vary according to the user's needs. Accordingly, it is to be understood that the present invention is not limited to the precise construction as shown in the drawings and described hereinabove.

I claim:

1. An irrigation control device comprising:
   at least one sprinkler valve;
   at least one soil moisture sensor for measuring the level of moisture in the soil surrounding the sensor, the sensor being inserted into the soil in close proximity to the sprinkler valve; and
   circuit means responsive to the sensor for initiating at least one pulsed sprinkler cycle when the soil moisture sensor detects a low soil moisture level, and repeating the cycle until the sensor detects a saturated soil condition, and further wherein the pulsed sprinkler cycle is comprised of the activation of the sprinkler valve for a first predetermined time period, and a subsequent deactivation of the sprinkler valve for a second predetermined period of time;
   said circuit means further comprising means for applying current to the soil moisture sensor, means for measuring a resultant current from the moisture sensor, a current to voltage converter for converting the measured resultant current to a converted voltage, a dry threshold voltage comparator for comparing the converted voltage to a predetermined high voltage level, and producing a dry soil signal when the converted voltage is higher than the predetermined high voltage level, a saturated threshold voltage comparator for comparing the converted voltage to a predetermined low voltage level, and producing a saturated soil signal when the converted voltage is lower than the predetermined low voltage, and means for initiating the pulsed sprinkler cycle in response to the dry soil signal, and for terminating the pulsed sprinkler cycle in response to the saturated soil signal.

2. An irrigation control device in accordance with claim 1 wherein the soil moisture sensor is comprised of two spaced apart conductive plates.

3. An irrigation control device in accordance with claim 1 wherein the circuit means further comprises a clock circuit, and further wherein the clock circuit controls the sprinkler cycle so that the first predetermined period of time is approximately one and one-half minutes, and the second predetermined period of time is approximately ten minutes.

4. An irrigation control device in accordance with claim 1 wherein the current applying means applies alternating current to the sensor.

5. An irrigation control device in accordance with claim 1 wherein a plurality of sensors are used, and a plurality of sprinkler valves are used, wherein at least one of the sprinkler valves corresponds to each of the sensors, and further wherein the circuit means further includes;
   an input selector for sequentially selecting one of the soil moisture sensors as a selected sensor;
   means for storing a low soil moisture signal indicating a low soil moisture condition and a saturated soil signal for indicating a saturated soil condition for the selected sensor;
   means for scanning the storage means for reading the signal stored for the selected sensor; and
   means for initiating the sprinkler cycle in response to reading a scanned stored low soil moisture signal, and repeating the cycle until a saturated soil signal is read.

6. An irrigation control device in accordance with claim 1 wherein the circuit means further comprises means for deactivating the device during the period of time after sunrise and before sunset.

7. An irrigation control device in accordance with claim 1 wherein the circuit means further comprises means for automatically deactivating the device when rainfall is detected.

8. An irrigation control device in accordance with claim 1 wherein the circuit means further comprises means for initiating at least one sprinkler cycle when a predetermined level of ambient heat is detected.

9. An irrigation control device in accordance with claim 1 wherein the circuit means further comprises a booster circuit for allowing low power operation of the sprinkler valve after the initial activation of the valve.

10. An irrigation control device in accordance with claim 1 wherein the device further includes a power supply, the power supply comprising:
    a plurality of nickel cadmium batteries; and
    a solar powered battery recharger.

11. A multichannel irrigation control system for an area having a plurality of zones comprising:
    a plurality of sprinkler valves, at least one of the sprinkler valves being located in each of the zones;
    a plurality of soil moisture sensors, at least one of the sensors being located in each of the zones, wherein each of the soil moisture sensors corresponds to one of the sprinkler valves;
    circuit means for monitoring the soil moisture sensors and selectively activating said sprinkler valves; said circuit means further comprising:
    an input selector for sequentially selecting one of the soil moisture sensors as a selected sensor;
    means for applying current to the selected sensor;
    means for measuring a resultant current from across the selected sensor;
    a current to voltage converter for converting the resultant current to a converted voltage;
    a dry threshold voltage comparator for comparing the converted voltage level to a predetermined high voltage level, and producing a dry signal when the voltage is higher than the predetermined high voltage level;
    a saturated threshold voltage comparator for comparing the converted voltage level to a predetermined low voltage level, and producing a saturated signal when the voltage is lower than the predetermined low voltage level;
    means for storing the dry signal and the saturated signal for the selected sensor;
    means for scanning the storage means for reading the stored signals; and
    means for initiating at least one pulsed sprinkler cycle in response to reading a scanned stored dry signal, and repeating the cycle until a saturated signal is read, and further wherein the pulsed sprinkler cycle is comprised of activation of the sprinkler valve for a first predetermined period of time, and a subsequent deactivation of the sprinkler valve for a second predetermined period of time.

12. An irrigation control system in accordance with claim 11 wherein said soil moisture sensors are each comprised of two spaced apart conductive plates.

13. An irrigation control system in accordance with claim 11 wherein the current applied to the sensors is an alternating current.

14. An irrigation control system in accordance with claim 11 wherein the circuit means further comprises means for deactivating the system during the hours after sunrise and before sunset.

15. An irrigation control system in accordance with claim 11 wherein the circuit means further comprises means for automatically deactivating the system when rainfall is detected.

16. An irrigation control system in accordance with claim 11 wherein the circuit means further comprises means for initiating at least one pulsed sprinkler cycle when a predetermined level of ambient heat is detected.

17. An irrigation control system in accordance with claim 11 wherein the circuit means further comprises a booster circuit for allowing low power operation of the valves after the initial activation of the valves.

18. A method of controlling an irrigation system comprising the steps of:
    inserting soil moisture sensors into the ground, the sensors being spaced apart conductive plates;
    installing at least one corresponding sprinkler in close proximity to each of the sensors;
    applying current across the plates of the soil moisture sensor;
    measuring the resulting current;
    converting the resulting current to a voltage;
    comparing the voltage to a predetermined dry voltage level to produce a dry signal when the voltage reaches the predetermined dry voltage level corresponding to undesired soil dryness;
    comparing the voltage to a predetermined saturation voltage level to produce a saturated signal when the voltage reaches the predetermined saturation voltage level corresponding to soil saturation;
    activating a pulsed sprinkler cycle when the dry signal is detected; and
    deactivating the pulsed sprinkler cycle when the saturated signal is detected.

19. A method of controlling an irrigation system in accordance with claim 18 wherein alternating current is applied across the plates.

* * * * *